United States Patent
Yamamoto et al.

(10) Patent No.: US 8,842,280 B2
(45) Date of Patent: Sep. 23, 2014

(54) ANALYTICAL APPARATUS AND DETECTION METHOD EMPLOYED IN ANALYTICAL APPARATUS

(75) Inventors: Shuhei Yamamoto, Mito (JP); Minoru Sano, Hitachinaka (JP); Akiyuki Nemoto, Mito (JP); Michiru Fujioka, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 134 days.

(21) Appl. No.: 13/519,228

(22) PCT Filed: Dec. 22, 2010

(86) PCT No.: PCT/JP2010/007408
§ 371 (c)(1),
(2), (4) Date: Sep. 13, 2012

(87) PCT Pub. No.: WO2011/080894
PCT Pub. Date: Jul. 7, 2011

(65) Prior Publication Data
US 2013/0017595 A1    Jan. 17, 2013

(30) Foreign Application Priority Data
Dec. 28, 2009 (JP) .................................. 2009-296655

(51) Int. Cl.
*G01N 21/00* (2006.01)

(52) U.S. Cl.
USPC ......................................................... 356/432

(58) Field of Classification Search
CPC ...................................................... G01N 21/00
USPC ......................................................... 356/432
See application file for complete search history.

(56) References Cited

U.S. PATENT DOCUMENTS

| 5,171,979 A | 12/1992 | Kwa et al. |
| 5,493,849 A | 2/1996 | Itoh |
| 2008/0047369 A1* | 2/2008 | Tsujimura et al. ......... 73/863.01 |

FOREIGN PATENT DOCUMENTS

| JP | 02-017449 A | 1/1990 |
| JP | 04-232870 A | 8/1992 |
| JP | 05-302927 A | 11/1993 |
| JP | 06-008995 A | 1/1994 |
| JP | 07-156994 A | 6/1995 |
| JP | 2003-075303 A | 3/2003 |
| JP | 2008-051531 A | 3/2008 |
| JP | 2009-204360 A | 9/2009 |

* cited by examiner

*Primary Examiner* — Roy M Punnoose
(74) *Attorney, Agent, or Firm* — Mattingly & Malur, PC

(57) ABSTRACT

Disclosed is an analytical apparatus wherein a container is automatically transferred and the container is automatically closed with a cap member, said analytical apparatus being provided with a suitable mechanism that reliably closes the container. The analytical apparatus is provided with an optical sensor composed of at least one pair of a light source (4) and a light detector (5), which face each other with the container disposing position therebetween, and which are disposed such that the container disposing position is irradiated with light, and the analytical apparatus detects whether the container (1) is disposed or not or the absence/presence of the cap of the container, corresponding to a transmitted light quantity detected by means of the optical sensor. Thus, cap closing is prevented from being performed if there is no container, and the container is prevented from being transferred without the cap.

11 Claims, 2 Drawing Sheets

FIRST SITUATION    SECOND SITUATION    THIRD SITUATION

ANALYTICAL APPARATUS AND DETECTION METHOD EMPLOYED IN ANALYTICAL APPARATUS

TECHNICAL FIELD

The invention relates to an analytical apparatus wherein a transfer of a container and a plugging with a cap are performed automatically.

TECHNICAL BACKGROUND

In an analytical apparatus performing automatically stages from mounting a specimen to a completion of analysis, there are cases wherein a container containing therein the specimen is transferred on the apparatus. For examples of the cases, there are the transfer to next one of the stages, stirring, centrifugal action, temperature control, measuring and so forth. In such analytical apparatus, the container is generally plugged to prevent a content from being discharged from the container during the transfer of the container. Particularly, in an analyzing technique wherein a contamination between the specimens is deemed as a problem, the containers need to be plugged hermetically.

For example, in an analytical apparatus performing a nucleic-acid amplification method such as typically PCR method wherein a nucleic-acid included by the specimen is amplified with a specific base sequence to detect the nucleic-acid of trace amount with high sensitivity, the contamination between the specimens is a significant problem, whereby the hermetical plugging of the containers is of necessary process. An nucleic-acid analyzing device with function of plugging containers on the apparatus is disclosed by, for example, JPA-2003-75303.

PRIOR ART DOCUMENTS

Patent Documents patent document 1: JP-A-2003-75303
patent document 2: JP-A-5-302927

SUMMARY OF THE INVENTION

Problem to be Solved by the Invention

The patent document 1 discloses a technique for plugging hermetically a container with pushing into the container a spherical plug. As mentioned above, since the contamination between the containers causes a significant effect on an analysis result in the nucleic-acid analyzing device, the plugging needs to be securely performed, but in the patent document 1, means for confirming as to whether the plugging has been securely performed is not disclosed, whereby a risk of the contamination by malfunction has not been solved. An object of the invention is to provide a mechanism suitable for performing the secure plugging in an analytical apparatus performing automatically the transfer of the container and the plugging with the cap.

Means for Solving the Problem

In an analytical apparatus with a function of plugging a container, the apparatus has a pair of a light source and a fiber optic sensor between which a container setting position is arranged, a light is emitted from the light source toward the container setting position, and (a) whether or not a container has been set, (b) whether or not a cap of the container exists, or (c) a degree of plugging is detected in accordance with a quantity of the transmitted light detected by the optical sensor so that success and failure of the plugging are monitored in each of process stages.

Effect of the Invention

According to the invention, in the analytical apparatus with the function of plugging the container, since success and failure of each of the process stages necessary for the plugging can be monitored, when a trouble occurs in the process stage, an appropriate treatment such as stopping immediately an analysis or the like can be performed, and a contamination caused by an malfunction in the plugging can be prevented before happens. Therefore, according to the invention, an analyzing environment of a high reliability without a contamination risk caused by a defect of the hermetic plugging, can be provided.

MODES FOR BRINGING THE INVENTION INTO EFFECT

In this embodiment, an analytical apparatus with a function of plugging a container, characterized in that the apparatus has an optical sensor comprised of a pair of a light source and a light detector between which a container setting position is arranged so that the container and a cap are irradiated with a light, and (a) whether or not a container has been set, (b) whether or not a cap of the container exists, or (c) a degree of the plugging is detected in accordance with a quantity of the transmitted light detected by the optical sensor, is disclosed.

Further, in this embodiment, the analytical apparatus wherein the quantities of the transmitted light output from at least one pair of the optical sensors are judged with a plurality of threshold values.

Embodiment 1

Figure 1:
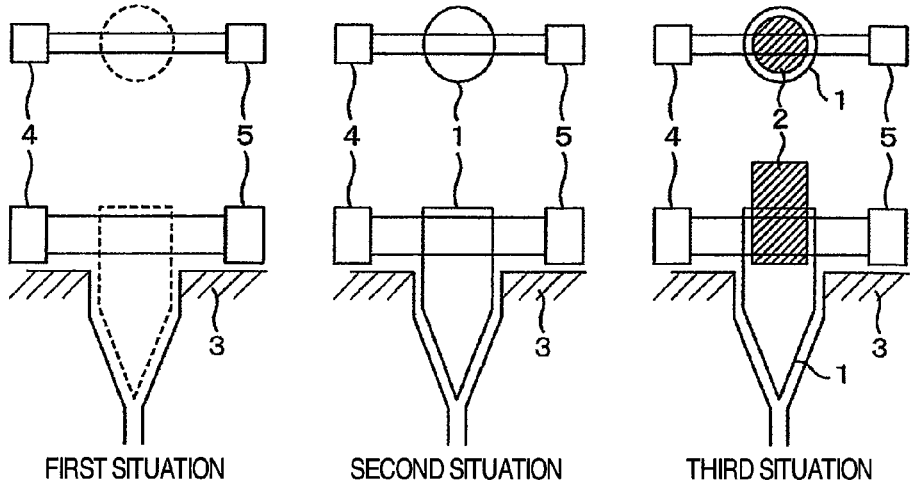
FIG. 1 Arrangement of a container, a cap member and an optical sensor (embodiment 1)
FIG. 2 Relationship between a quantity of transmitted light and a condition of plugging (embodiment 1)
FIG. 3 Arrangement of a container, a cap member and an optical sensor (embodiment 2)
FIG. 4 Arrangement of the container, the cap member and the optical sensor (embodiment 2)
FIG. 5 Arrangement of a container, a cap member and an optical sensor (embodiment 3)

An embodiment of the invention is explained with using FIG. 1. In FIG. 1, in order from left hand, three situations, a first situation wherein a container 1 has not been mounted on a container mounting table 3, a second situation wherein the container 1 is mounted on the container mounting table 3 before being plugged, and a third situation wherein the container 1 is mounted on the container mounting table 3 and plugged with a cap member 2, are shown. FIG. 1 includes plan views at its upper side, and cross-sectional views at its lower side.

The container 1 is for containing a specimen or a reagent. Its material is preferably a resin of optical transparency, or a glass. Another material which is not completely opaque in a wave length range of a light emitted from a light source for detecting the container 1 and the cap member 2 as mentioned below, or whose optical transmittance is not nearly 100%, is usable. For example, a transparent or semi-transparent PCR tube of polypropylene resin is preferable.

The cap member 2 is used to hermetically plug the container 1. Its shape needs to be capable of hermetically plugging the container 1, and a portion thereof closely contact the container 1 may be arranged at any one of inside and outside of the container. Its shape is preferably spherical or column-shaped when contacting hermetically the inside of the container, and is preferably cylindrical when contacting hermetically the outside of the container. A material thereof is preferably a resin, glass or metal. A transparency of the cap member 2 is preferably equivalent to or not more than that of the container 1, and is preferably as low as possible. In the embodiment of FIG. 1, the cap member 2 made of the resin and having the semi-transparent column-shape is pressed downwardly into the container 1 to be plugged.

An optical sensor for detecting the container 1 and the cap member 2 is composed of a light source 4 and a light detector 5. The optical sensor wherein the light source 4 and the light detector 5 are combined may be used, or the optical sensor wherein the light source 4 and the light detector 5 are arranged independent of each other may be used. The light source 4 and the light detector 5 are arranged to face to each other through the container so that a light from the light source is detected by the light detector. Further, the light emitted from the optical sensor 4 is arranged so that a region where the container 1 and the cap member 2 overlap each other is irradiated by the light.

In the first situation, the light emitted from the light source 4 reaches directly the light detector 5.

In the second situation, the light emitted from the light source 4 passes through the container 4 to decrease its intensity, and subsequently reaches the light detector 5, whereby the quantity of the transmitted light is decreased in comparison with the first embodiment.

In the third situation, the light emitted from the light source 4 passes through both of the container 4 and the cap member 2, and subsequently reaches the light detector 5, whereby the quantity of the transmitted light is further decreased in comparison with the second embodiment.

Figure 2:
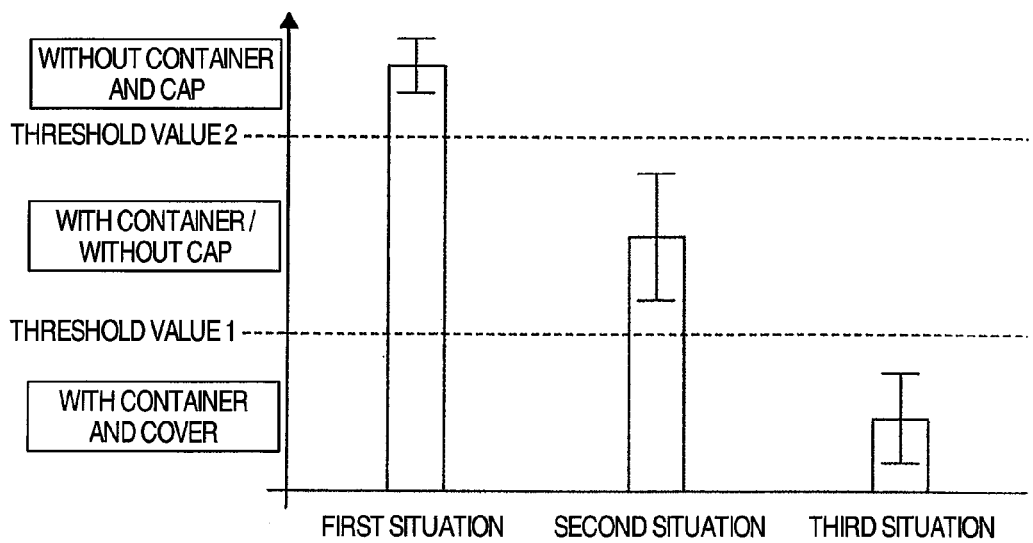

FIG. 2 is a graph showing an example of the quantities of the transmitted lights detected by the first to third situations. Bar graph shows an average value of the quantity of the transmitted light at each of the situations. A fluctuation range including individual differences in optical transmittance between the containers 1 and between the cap members 2, a repeatability of measuring and so forth is indicated by an error bar. When combination values of the quantities of the transmitted lights and the fluctuation ranges at the respective situations do not overlap each other, the situations can be differentiated from each other on the basis of a threshold value 1 and a threshold value 2.

By differentiate the above three situations from each other, the plugging can be performed securely. For example, by controlling the cap member 2 to be prevented until the second situation is detected from being transferred onto the container 1, the cap member 2 can be securely mounted onto the container 1. Further, by controlling the container 1 to be prevented until the third situation is detected from being transferred, a transfer of the container with incomplete plugging as well as a dispersion of the content caused thereby are prevented, and a risk of the contamination can be significantly decreased.

Incidentally, each of the detected situations may be shown on a display to inform a user of the detected situation.

Embodiment 2

The plugging conditions may be differentiated by using a plurality of the threshold values with an optical signal from a pair of the optical sensor as shown in FIG. 1, or may be differentiated by using a plurality of the pairs of the optical sensors having the respective threshold values different from each other. A second embodiment is explained with using FIG. 3 and FIG. 4.

Figure 3:
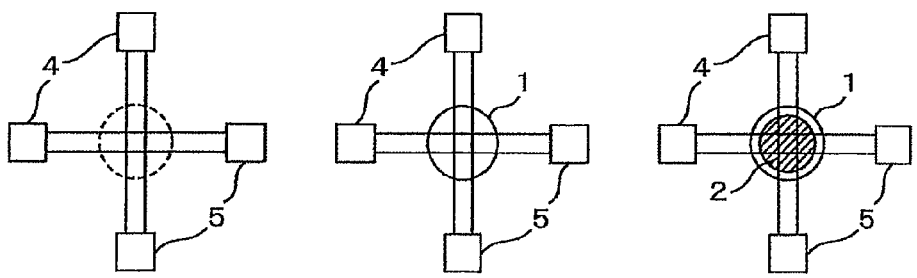
Figure 4:
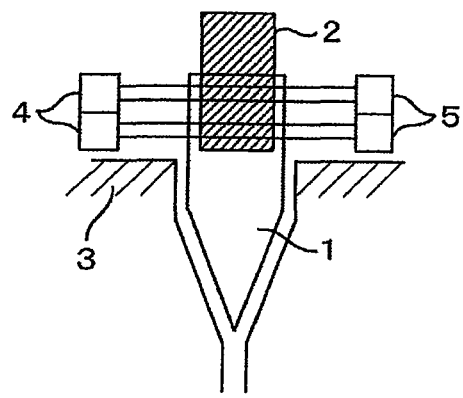

FIG. 3 shows the embodiment wherein two pairs of the optical sensors having the respective threshold values different from each other are arranged to be perpendicular to each other on a common plane. By setting each of the threshold values in a manner similar to the first embodiment, the three plugging conditions can be differentiated from a combination of the outputs of both of the sensors, similarly to the first embodiment. The two pairs of the optical sensors may be arranged to have an angle other than a right angle. Further, the two pairs of the optical sensors may be arranged at respective heights different from each other, rather than on the common plane. The arrangement may be determined appropriately in accordance with the used sensor's shape, size, space with respect to a circumjacent mechanism, and so forth.

Embodiment 3

Figure 5:
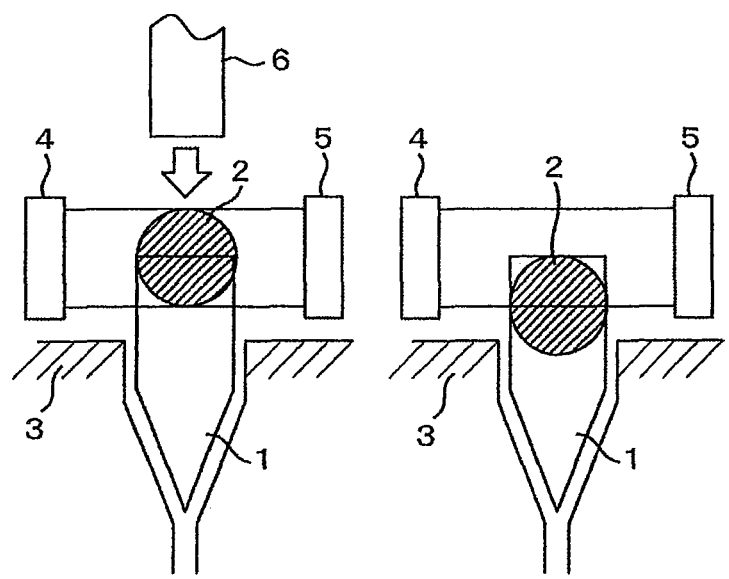

The situations more than the first to third situations explained in the first and second embodiments can be differentiated with using the similar principle. A third embodiment of the invention is explained with using FIG. 5. In the embodiment of FIG. 5, a spherical resin cap is used as the cap member 2. This cap member is pressed by a pressing mechanism 6 into the container to be plugged. A left side of FIG. 5 shows a situation wherein the cap member 2 is mounted on the container 1 while awaiting being pressed by the pressing mechanism 6, and a right side of FIG. 5 shows a situation wherein the cap member 2 is pressed into the container 1 to complete the plugging. By arranging a pair of area detection fiber optic sensors to be capable of irradiating the cap member 2 at both of these two situations as shown in FIG. 5, these two situations can be differentiated from each other in accordance with a difference in quantity of the transmitted light therebetween. In a case of that the pressing-in operation is brought about before the cap member 2 has been mounted, the pressing mechanism contacts the specimen of liquid adhering to an inner wall of the container 1 to cause a problem of that the specimen to be treated in future is contaminated thereby. By confirming the above two situations, this problem is avoided. In a case of that the situation wherein the container has not been mounted as well as the situation wherein the container has been mounted but the cap member 2 has not been mounted are confirmed, the pair of the optical sensors can differentiate four as a total of the situations from each other, a control for preventing the contamination can be performed more precisely.

Incidentally, as a method for differentiating the two situations of FIG. 5 from each other, for example, two pairs of the optical sensors may be arranged to be vertically juxtaposed to each other, other than the area sensor shown as the present embodiment.

EXPLANATION OF DENOTING SIGNS 1 container
2 cap member 3 container mounting table
4 light source
5 light detector
6 pressing-in mechanism

The invention claimed is:

1. An analytical apparatus with a function of plugging a container with a cap, comprising:
    an optical sensor having at least one pair of a light source and a light detector between which a container setting position is arranged so that the cap is irradiated with light both in a situation where the cap is mounted on the container and in a situation where the cap is pressed into the container to complete the plugging,
    wherein an optical transmittance of the cap is less than an optical transmittance of the container, and
    wherein whether or not the container has been set, the cap exists on the container, the cap is mounted on the container, and the cap is pressed into the container to complete the plugging are detected in accordance with a quantity of transmitted light detected by the optical sensor.

2. The analytical apparatus according to claim 1, wherein the quantity of transmitted light output from the optical sensor is judged with respect to a plurality of threshold values.

3. The analytical apparatus according to claim 2, wherein the plurality of threshold values includes,
    a first threshold value for judging whether or not the container has been set at the container setting position, and
    a second threshold value for judging whether or not the cap set at the container setting position has been plugged by the cap.

4. The analytical apparatus according to claim 1, wherein the optical sensor is a fiber sensor.

5. The analytical apparatus according to claim 1, wherein whether or not the container has been set, the cap exists on the container, the cap is mounted on the container, and the cap is pressed into the container to complete the plugging are displayed on a display.

6. The analytical apparatus according to claim 1, wherein the optical sensor is an area sensor.

7. The analytical apparatus according to claim 1, wherein the optical sensor has two pairs of light sources and light detectors arranged to be vertically juxtaposed to each other so that the cap is irradiated with light both in the situation where the cap is mounted on the container and in a situation where the cap is pressed into the container to complete the plugging is irradiated with light, and
    wherein the detecting is performed in accordance with a quantity of transmitted light detected by the two pairs of light sources and light detectors.

8. The analytical apparatus according to claim 7, wherein the two pairs of light sources and light detectors have respective threshold values different from each other.

9. A detecting method to be used in an analytical apparatus with a function of plugging a container with a cap, comprising:
    irradiating a container setting position with an optical sensor having at least one pair of a light source and a light detector between which the container setting position is arranged so that the cap is irradiated with light both in the situation where the cap is mounted on the container and in the situation where the cap is pressed into the container to complete the plugging; and
    detecting whether or not the container has been set at a container setting position, the cap exists on the container, the cap is mounted on the container, and the cap is pressed into the container to complete the plugging in accordance with a quantity of transmitted light detected by the optical sensor.

10. The detecting method according to claim 9, wherein the optical sensor is an area sensor.

11. The detecting method according to claim 9, wherein the optical sensor has two pairs of light sources and light detectors arranged to be vertically juxtaposed to each other so that the cap is irradiated with light both in the situation where the cap is mounted on the container and in the situation where the cap is pressed into the container to complete the plugging, and
    wherein the detecting is performed in accordance with a quantity of transmitted light detected by the two pairs of light sources and light detectors.

* * * * *